(12) United States Patent
Håkansson et al.

(10) Patent No.: US 6,761,885 B1
(45) Date of Patent: Jul. 13, 2004

(54) STRAIN OF LACTOBACILLUS PLANTARUM AND USES THEREOF

(75) Inventors: Eva Grahn Håkansson, Umeå (SE); Ulla Forsgren-Brusk, Pixbo (SE); Rolf Andersson, Mölnlycke (SE); Stig E. Holm, Umeå (SE); Stellan Håkansson, Umeå (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/623,562
(22) PCT Filed: Mar. 5, 1999
(86) PCT No.: PCT/SE99/00336
  § 371 (c)(1),
  (2), (4) Date: Nov. 16, 2000
(87) PCT Pub. No.: WO99/45099
  PCT Pub. Date: Sep. 10, 1999

(30) Foreign Application Priority Data

Mar. 6, 1998 (SE) .............................................. 9800749
Jun. 2, 1998 (SE) .............................................. 9801951

(51) Int. Cl.[7] ............................................. A01N 63/00
(52) U.S. Cl. .................... 424/93.45; 424/430; 424/431; 424/433; 604/360
(58) Field of Search .............................. 424/93.45, 430, 424/431, 433; 604/360

(56) References Cited

U.S. PATENT DOCUMENTS 5,645,830 A * 7/1997 Reid et al. ................ 424/93.45
5,705,160 A   1/1998 Bruce et al.

FOREIGN PATENT DOCUMENTS

| EP | 0353581 A2 | 9/1990 |
| FR | 2656798 A1 | 7/1991 |
| WO | WO 84/04675 | 12/1984 |
| WO | WO 93/09793 | 5/1993 |
| WO | 97/02846 * | 1/1997 |
| WO | WO 9729762 | 8/1997 |

* cited by examiner

Primary Examiner—Irene Marx
(74) Attorney, Agent, or Firm—Young & Thompson (57) ABSTRACT

A novel strain of *Lactobacillus plantarum*, referred to as LB931, has now been isolated. The strain has been deposited at Deutsche Sammlung von Mikroorganismen, Braunschweig, DE. It has been assigned accession number DSM11918. Accordingly LB931 can be used for treating and/or preventing urogenital infections. LB931 can advantageously be included in pharmaceutical compositions and in products for personal care, such as feminine hygiene products, diapers and sanitary napkins.

20 Claims, 4 Drawing Sheets

Stability test, LB 931 (lyophilised)

STRAIN OF *LACTOBACILLUS PLANTARUM* AND USES THEREOF

The present invention relates to a novel Lactobacillus strain, which possesses valuable pharmaceutical characteristics. The invention also relates to pharmaceutical compositions and products for personal care comprising the strain, as well as use of the strain for prevention of urogenital infections.

TECHNICAL BACKGROUND (All citations in the following description are incorporated by reference).

The usual bacterial flora in the urogenital region in constituted by a complex eco-system comprising more than 50 different bacterial species (Hill et al., Scand. J. Urol. Nephrol. 1984;96 (suppl.):23–29). The normal flora is dominated by bacteria belonging to the genus Lactobacillus (LB) which are Gram positive rods adapted to the environment in the vagina of the fertile woman. These bacteria also contribute to the maintenance of the specific milieu and the ecological balance in the vagina.

Beside the complex interaction pattern of the multitudinous bacterial flora of the vagina and the rest of the urogenital region, it is necessary to consider the variation of physical conditions that can influence bacterial growth and adhesion properties. Some LVS strains inhibit growth of potentially pathogenic bacteria by various mechanisms. The metabolism of LB results in formation of organic acids, above all lactic acid and acetic acid, which contribute to the low pH of vaginal fluid which is unfavourable for many other species. LB may also produce soluble substances which directly inhibit growth of potentially pathogenic bacteria and yeast. They can also produce hydrogen peroxide which is toxic to bacteria lacking the enzyme catalase, such as gram-negative anaerobic rods and Enterobacteriacae. These inhibiting characteristics may vary considerably between different LB strains (Hooton et al., JAMA 1990; 265:64–69).

Weakness of the natural deference system may allow potentially pathogenic micro-organisms to cause clinical infection, for example in connection with medication, inferior personal care, or shifts in the microflora of skin or mucous membranes. The normal flora of the vagina is dominated by LB and the surrounding pH is lower than 4.5. Yeast and enterobacteria are scanty or absent (Redondo-Lopez et al., Rev. Inf. Dis. 1987; 12:856–872). Shifts of the vaginal bacterial flora can be found in connection with different pathogenic conditions. There is an increased amount of enterobacteria in the vagina and urethral orifice of women suffering from recrudescent urinary tract infections and they also have a urogenital flora depleted of lactobacilli (Marrie et al. J. Clin. Microbiol. 1976, 8, 67–72). It is also known that the frequency of infections increase in connection with antibiotic treatment of other infections (Stamey, Rev. Inf. Dis. 1987; 9(suppl. 2):195–208; Reid et al., Curr. Opin. Inf. Dis. 1991; 4:37–41). In addition, it has been demonstrated that children who have a history of frequent episodes of antibiotic treatment are more prone to contract urinary tract infections (Mårild et al., Ped. Inf. Dis. 1990; 22:43–47).

In bacterial vaginosis the amount of LB is decreased and pH is increased. There is also a dominance of Bacterioides species, *Gardnerella vaginalis* and *Mobiluncus* (Redondo-Lopez, supra). Vaginitis, associated with an increased amount of entero-bacteria, is often a tangible problem in connection with antibitotic treatment. Common oral administration of penicillin results in the accumulation of the substance in vaginal fluid (Sjöberg et al., Obstet. Gynecol. 1990; 75:18–21) followed by colonisation by enterobacteria and yeast (Sjöberg et al., Gynecol. Obstet. Invest. 1992; 33:42–46). Investigations in monkeys (*Macaca fascicularis*) have revealed that vaginal administration of amoxicillin impairs the ability of the normal bacterial flora to inhibit colonisation of urinary tract-pathogenic *E. coli* (Herthelius et al., Infection 1988; 16:263–266).

During pregnancy the composition of the vaginal flora may influence the morbidity of the fetus and child. Occurence of group B streptococci (GBS) in the faecal and vaginal flora is common (up to 30% of all pregnant women). These bacteria do not normally constitute a threat to the woman's health. However, GBS may cause serious infections in the new-born child. In these cases, bacteria are transmitted vertically from mother to child before or in connection with birth. Other bacteria can also be transmitted in this way and cause infections in the child. There is also a strong connection between bacterial vaginosis and premature birth (Martius et al., Arch. Gynecol. Obstet. 1990; 247:1–13). The mechanisms behind this phenomenon are not known. It has been shown that a shift of the vaginal flora towards dominance of Gram negative species increases the amount of the enzyme phospholipase A2, which in turn may initiate prostaglandin synthesis starting from arachidonic acid (Bejar et al., Obstet. Gynecol. 1981; 57:479–482). The vaginosis flora also produces large amounts of endotoxin (Sj öberg et al., Obstet. Gynecol. 1991; 77:265–266), which may induce endogenous prostaglandin synthesis (Romero et al., Obstet. Gynecol. 1989; 73:31–34), possibly mediated by interleukines.

The theoretically positive characteristics of LB have motivated their use in commercial preparations with the intend use to supplement and strengthen the vaginal flora. Success has been variable and often the available preparations contain considerably lower numbers of LB than what has been stated. Some preparations have also been contaminated (Hughes et al., Obstet. Gynecol., 1990; 75(2):244–248). In order to supplement and improve the normal bacterial flora in the urogenital region by addition of LB, it is necessary to carefully select the bacterial strains to be used. A LB strain that is suitable for this purpose should fulfil the following criteria.

1. The LB strain should produce high amounts of soluble substances with growth inhibiting capacity on enterobacteria, group B streptococci, staphylococci and yeast.
2. The LB strain should be able to be transferred to skin and mucosal surfaces of the urogenital region.
3. The LB strain should be able to adhere to epithelial surfaces in the urogenital region.
4. The LB strain should be able to endure storage for a long period of time, and it must be possible to induce the strain in different kinds of preparations.
5. The LB strain should be able to retain its viability and characteristics in an article or preparation upon use.
6. The LB strain should not be sensitive to spermicidal preparations containing nonoxynol-9.
7. The LB strain should be isolated from the urogenital tract of human female.
8. The LB strain should permit existence of the human urogenital LB flora.

Therefore, there is a demand for strains, fulfilling these requirements.

SUMMARY OF THE INVENTION

A novel strain of *Lactobacillus plantarum*, referred to as LB931, has been isolated, which fulfils requirements listed above. The strain has been deposited on Jan. 27, 1998 at Dsmz-Deutsche Sammlung von Mikroorganisem und Zeelkultren, Mascheroder Weg 1b D-38124 Braunschweig. It has been assigned accession number DSM11918. Accordingly LB931 may be used for treating and/or preventing urogenital infections. LB931 can advantageously be included in pharmaceutical compositions and in products for personal care, such as diapers and sanitary napkins.

Definitions

As disclosed herein, the term "LB" refers to bacteria of the genus Lactobacillus.

As disclosed herein, the term "Urogenital region" refers to perineum, urethra and vagina.

As disclosed herein the term "absorbent article" relates to products suitable for absorbing a body fluid, such as blood or urine. Examples of such articles are feminine hygiene products, incontinence guards, and diapers.

As disclosed herein, the term "GBS" refers to group B Streptococcus.

As disclosed herein, the term "lactic acid bacteria" relates to bacteria producing lactic acid, such as bacteria belonging to the genera Lactobacillus and Lactococcus.

By the term "cfu" is meant colony-forming units.

DETAILED DESCRIPTION OF THE INVENTION

The present invention relates to a novel strain of *Lactobacillus plantarum*, referred to as LB931 (DSM11918). This bacterial strain is valuable for preventing and/or treating urogenital infections as it inhibits growth of a large number of pathogenic micro-organisms. The strain is endurable and readily survives long periods of storage in room temperature. Accordingly products containing LB931 have a long shelf life. The strain can easily be transferred to the human skin and vaginal epithelium. LB931 is resistant to therapeutic concentrations of some antibiotic substances and spermacidal compounds.

The inhibition characteristics of LB931 has been investigated. Examples of bacteria species which are successfully inhibited are Escherichia, Klebsiella, Proteus, Staphylococcus and group B Streptococcus. LB931 is therefore useful for preventing and/or treating infections caused by these micro-organisms.

As noted above, the present invention also provides a variety of pharmaceutical compositions, preferably suitable for topical administration, comprising LB931 along with pharmaceutically or phsyiologically acceptable carriers, excipients and/or diluents. Generally, such carriers should be non-toxic to recipients at the dosages and concentrations employed. Normally, the preparation of such compositions entails the combination of the therapeutic agent with buffers, thickening agents of gel-forming agents such as glycerine, polyethylene glycol, etc. Antioxidants such as ascorbic acid, low molecular weight (less than about 10 residues) polypeptides, proteins, carbohydrates including glucose, sucrose and dextrins, and other stabilisers and excipients may be included. Possible pharmaceutical compositions are ointments, creams, liquid solutions, suppositories or capsules.

The present invention also relates to absorbent articles comprising LB931. Such an article may include a permeable outer sheet which is intended to be in close contact with the skin of the wearer, a preferably liquid-impermeable backing sheet which is intended to lie distal from the wearer in use, and an absorbent structure arranged between the outer sheet and the backing sheet. In some cases, an additional sheet in the form of e.g. wadding or like material, may be placed between the outer sheet and the absorbent structure. The micro-organisms exhibiting antagonistic properties may be arranged in different parts of the absorbent article, for instance in the outer sheet, in the absorbent structure of the absorbent article, between two of the layers of the absorbent article, in a loose insertproduct in the absorbent article, or in some other way.

The present invention will now be described with reference to the enclosed figures in which.

The present invention will now be described with reference to the following examples:

EXAMPLE 1

Isolation and Typing of *Lactobacillus plantarum*, Strain LB931

Bacterial samples were taken from healthy women. From these samples, bacterial strains were isolated and these strains were screened on the basis of their ability to inhibit growth of enterobacteria (data not shown). The best strain, isolated from a healthy pregnant woman, was classified as *Lactobacillus plantarum* according to the test kit API 50 CH (API systems, BioMerieux, FR), and was denominated LB931. The strain was further typed by DNA-analysis with SDS-page at BCCM/LMG (Belgium) to be *Lactobacillus plantarum-pentosus-paraplantarum*.

EXAMPLE 2

Inhibition Capacity of Strain LB931

The purpose of this experiment was till illustrate the ability of strain LB931 to inhibit growth of other bacteria. LB931 was grown in MRS broth (Merck, DE) at a temperature of 37° C. in 5% $CO_2$ over night. One ml, containing $10^8$ bacteria was added to 25 ml of melted 2% agar in MRS-broth. The mixture was poured into the Petri dish, allowed to congeal and incubated as described above for 24 hours. Another 25 ml of M17-agar (Merck, DE) was poured on top of the first layer and the plates were left at room temperature for 4 hours. Similar agar plates without LB931 were also made and used as control plates.

The indicator bacteria were cultured separately in TY-medium (Holm et al., APMIS 1967; 69, 264) at 37° C. in air. The cultures were transferred to a 25 compartment Bertani tray, each compartment holding 0.25 ml ($10^6$ bacteria/ml). From each of these trays the bacteria were transferred and stamped onto the agar plates containing the Lactobacillus, using the Steer's steel pin replicator (Steers et al. J. Antibiot. Chemother. 1979, 9, 307). The plates were incubated in 37° C. overnight. The plates were read and it was established whether a) the indicator bacteria had grown; b) the growth of the indicator bacteria had been inhibited; or c) no growth of the indicator bacteria had occurred. The pH of each of the plates were also monitored.

The results of the interference tests are shown in table I.

TABLE I

| Indicator bacterial sp. | Inhibition | |
|---|---|---|
| | % | No/total |
| Coagulase negative staphylococci | 90 | 9/10 |
| Group B streptococcus sp. | 100 | 19/19 |
| Lactobacillus sp. | 7 | 1/14 |
| Klebsiella sp. | 100 | 50/50 |
| E. coli | 100 | 50/50 |
| Proteus sp. | 100 | 50/50 |

The results show that *Lactobacillus plantarum*, LB931 inhibits or prevents growth of a large number of bacterial strains, and that other Lactobacillus strains are mostly unaffected.

EXAMPLE 3

The Survival Capabilities of LB931 in Different Preparations a) LB931 dissolved in a suspension of equal parts skim milk and 0.9% NaCl LB931 was dissolved in skim milk containing 0.9% NaCl. The dissolved bacteria was then incubated at different temperatures. The amount of bacteria was continuously monitored by cell counting. The results are disclosed in table II below.

TABLE II

| | No. of bacteria (CFU) | | | |
|---|---|---|---|---|
| Temperature (° C.) | Day 0 | Day 2 | Day 5 | Day 32 |
| 4 | 7.8 × 10$^{10}$ | | | 2.2 × 10$^{10}$ |
| 20 | 1.8 × 10$^{10}$ | | 2.2 × 10$^{10}$ | |
| 27 | 1.8 × 10$^{10}$ | 1.2 × 10$^{10}$ | 3.3 × 10$^9$ | |
| 37 | 1.8 × 10$^{10}$ | 5.8 × 10$^9$ | 1.0 × 10$^5$ | |

The results show that LB931 is stable in a mixture of skim milk and NaCl for a period of one month at +4° C.

b) A skim milk preparation of LB931 was freeze-dried according to standard methods. The obtained powder was stored in Petri dishes at room temperature and at +6° C. The number of bacteria was determined after 7 days and 25 days, respectively. The results are disclosed in table III below.

TABLE III

| | No. of bacteria (CFU) | | |
|---|---|---|---|
| Temperature (° C.) | Day 0 | Day 7 | Day 25 |
| 6 | 4.2 × 10$^8$ | 2.2 × 10$^8$ | 1.2 × 10$^8$ |
| 22 | 4.2 × 10$^8$ | 1.9 × 10$^8$ | 1.4 × 10$^8$ |

Figure 1:
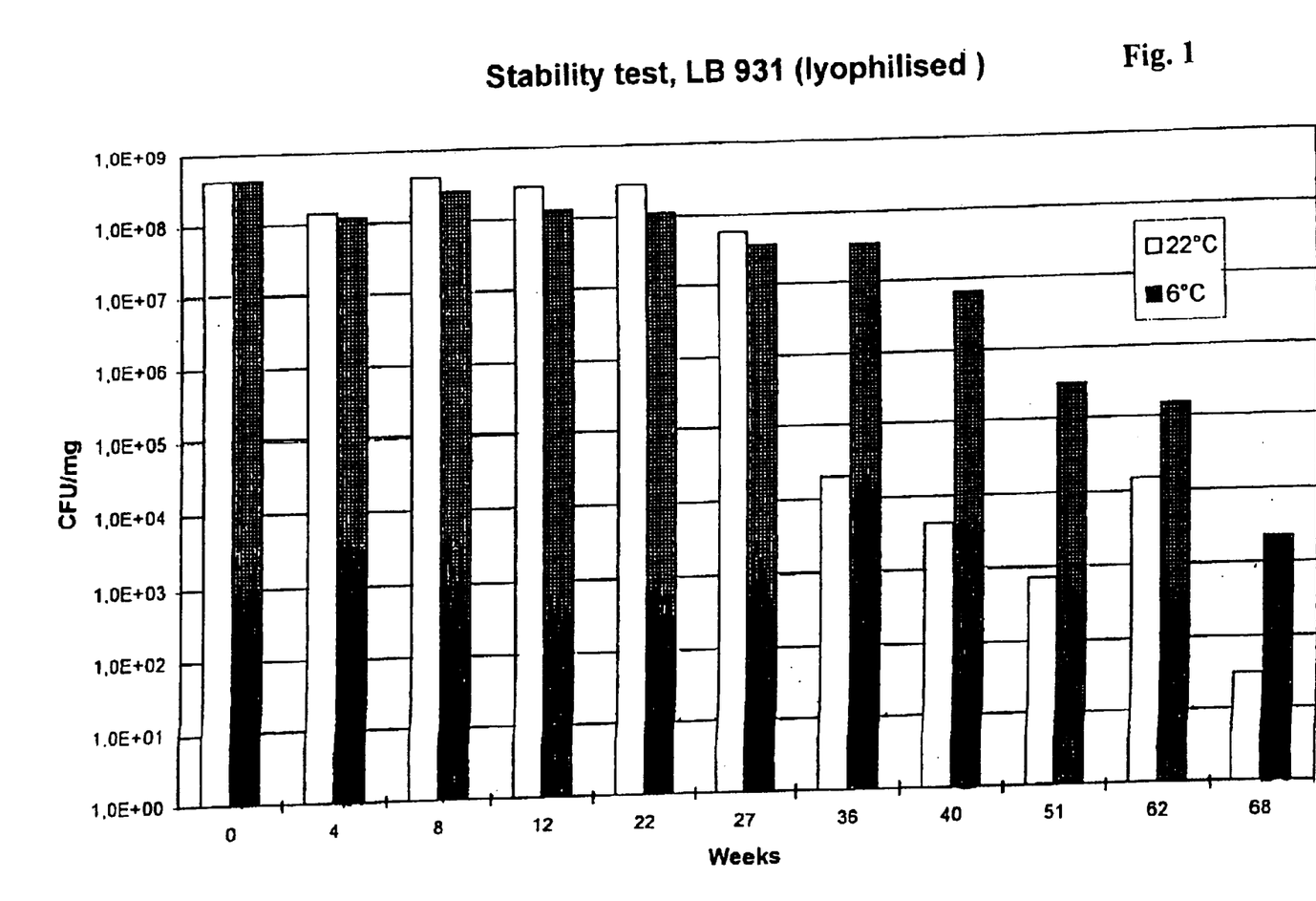
FIG. 1 is a diagram showing the stability of freeze-dried LB931 at room temperature (+22° C.) and at +6° C.
Figure 2:
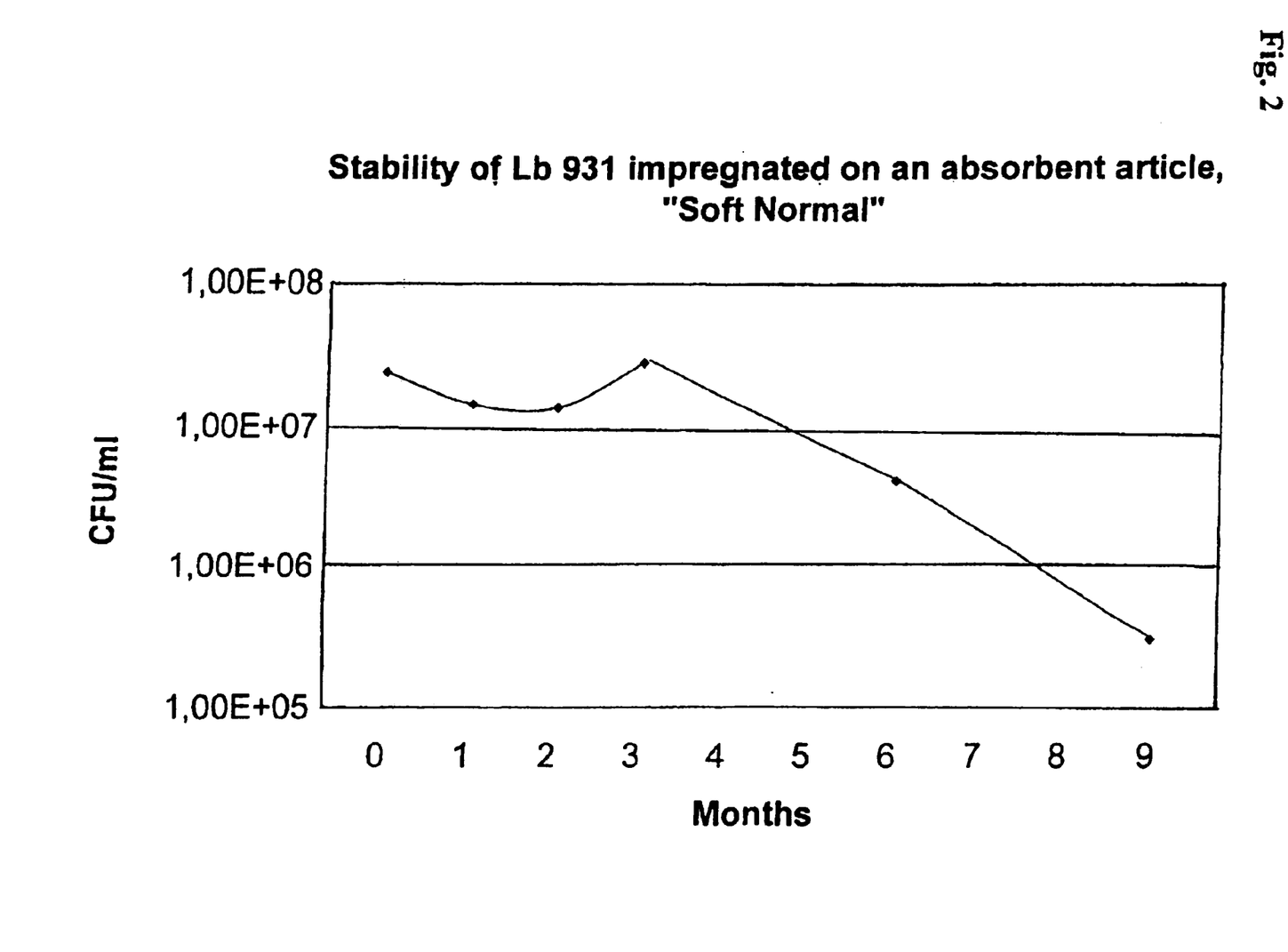
FIG. 2 is a diagram showing the stability of LB931 impregnated on an absorbent article.

The number of bacteria in the freeze-dried powder was also monitored every fourth week up to 68 weeks. These results are presented in FIG. 1. It is evident from the figure that LB931 is stable both at room temperature and +6° C. for 22 weeks. After one year, at +6° C., more than 10$^5$ cfu/mg LB931 is viable.

c) The ability of LB931 to survive in synthetic urine, pH 6.6, was tested. The synthetic urine contains mono-, a divalent cat- and anions as well as urea and was prepared acc to specifications in Geigy, Scientific Tables, vol. 2, 8:th ed. 1981 p 53. To the sterile synthetic urine, nutrient medium for microorganisms was added. The nutrient medium was prepared according to data from the composition of Hook- and FSA-media. To 1 ml of synthetic urine 10$^3$ LB931 bacteria were added, and the samples were incubated for 18 h at 32° C. After incubation the number of bacteria in the sample was >10$^5$/ml. LB931 is able to survive and grow in synthetic urine.

d) The ability of LB931 to survive on an absorbent article (panty liner) was investigated. A suspension of LB931 (150 µl) was added to the absorbent article, and this article was subsequently stored in a tight package up to 9 months. The results are shown in FIG. 2. A great number of bacteria survived for seven months.

e) Finally the LB931 was tested about its characteristics over a period of growth and storage. LB931 was cultivated in MRS-broth and a new passage was made every third day for three months. After that the start sample of LB931 and the last passage was compared in the API-test, PGFE and interference test. The two samples were identical in all the tests. This shows that LB931 is very stable after storage and several passage in growth medium.

EXAMPLE 4

Transfer of LB931 to Perineum Skin and Urethral Orifice in Woman

In order to study transfer of LB931 to perineum when using a pantry liner, the following investigation was carried out. All test persons were women between 12 and 60 years of age, and the tests were carried out between menstrual periods when appropriate. Test products were manufactured from conventional panty liners comprising a liquid-permeable outer layer, a liquid-impermeable rear-side layer an in between an absorbent layer of 100–200 g/m$^2$ of chemical cellulose pulp. On the absorbing side of the test product a suspension of LB931 bacteria was sprayed in an amount of 10$^9$ colony-forming units a product.

In order to determine the presence of LB931 in perineum of the 13 test persons, a so called swab test was carried out. Bacteria were collected by rubbing a sterile stick comprising a cotton tip which has been immersed into sterile sodium chloride solution on to a defined skin area. The occurrence of LB931 and other LB on perineal skin and at the urethral orifice were determined. The test persons were determined in this manner in order to establish a blank sample. Then, the test persons wore the panty liner during hours in the morning. The panty liner was removed and the occurrence of added lactic acid bacteria and natural lactic acid bacteria, respectively, was determined again, directly after removing the panty liner. This sample was referred to as sample 1. After 4–5 more hours a further sample was taken, and was referred to as sample 2. The lactic acid bacteria type was identified using Rogosa-agar with vancomycin for LB931 and Rogosa-agar plates incubated anaerobic for other LB. Further identification was done by API (BioMerieux, FR) and PFGE (pulsed field electrophoresis). The results are shown in table IV. LB931 could be found on perineum skin or urethral orifice in all women after using panty-liner sprayed with LB931.

TABLE IV

| Person No. | | Sample 1 | | Sample 2 | |
|---|---|---|---|---|---|
| | | Urethral orifice | Perineal skin | Urethral orifice | Perineal skin |
| 1 | Lb931 | $2 \times 10^2$ | $4 \times 10^4$ | 0 | 0 |
| | Endogenous LB flora | 0 | 0 | 0 | 0 |
| 2 | Lb931 | $6 \times 10^1$ | $7 \times 10^3$ | 0 | $2 \times 10^2$ |
| | Endogenous LB flora | 0 | 0 | 0 | 0 |
| 3 | Lb931 | $1 \times 10^3$ | $1 \times 10^2$ | $1 \times 10^1$ | $5 \times 10^1$ |
| | Endogenous LB flora | 0 | 0 | 0 | 0 |
| 4 | Lb931 | $1 \times 10^2$ | $3 \times 10^2$ | $3 \times 10^1$ | $1 \times 10^3$ |
| | Endogenous LB flora | + | + | + | 0 |
| 5 | Lb931 | $2 \times 10^3$ | $3 \times 10^3$ | $2 \times 10^1$ | $1 \times 10^1$ |
| | Endogenous LB flora | + | + | + | 0 |
| 6 | Lb931 | $1 \times 10^3$ | $2 \times 10^2$ | $1 \times 10^1$ | $7 \times 10^1$ |
| | Endogenous LB flora | + | + | + | + |
| 7 | Lb931 | $2 \times 10^3$ | $8 \times 10^3$ | $1 \times 10^2$ | $7 \times 10^1$ |
| | Endogenous LB flora | + | + | + | + |
| 8 | Lb931 | $2 \times 10^1$ | $4 \times 10^3$ | 0 | $8 \times 10^1$ |
| | Endogenous LB flora | + | + | 0 | 0 |
| 9 | Lb931 | $9 \times 10^1$ | $2 \times 10^3$ | 0 | $8 \times 10^1$ |
| | Endogenous LB flora | + | + | + | + |
| 10 | Lb931 | $3 \times 10^3$ | $2 \times 10^4$ | $7 \times 10^2$ | $4 \times 10^3$ |
| | Endogenous LB flora | 0 | 0 | 0 | 0 |
| 11 | Lb931 | $2 \times 10^3$ | $6 \times 10^2$ | $3 \times 10^2$ | $2 \times 10^2$ |
| | Endogenous LB flora | + | + | + | + |
| 12 | Lb931 | $7 \times 10^1$ | $9 \times 10^2$ | 0 | $1 \times 10^1$ |
| | Endogenous LB flora | 0 | 0 | 0 | 0 |
| 13 | Lb931 | $5 \times 10^3$ | $7 \times 10^3$ | $7 \times 10^2$ | $7 \times 10^1$ |
| | Endogenous LB flora | 0 | 0 | 0 | 0 |
| | No Lb931 positive: | 13 | 13 | 8 | 12 |

EXAMPLE 5

Transfer of LB931 to Perineum Skin and Urethral Orifice in Girls

Thirteen young girls between 3 and 12 years old were included in study. Bacterial samples from the perineal skin and urethral orifice were obtained by first immersing a cotton swab in MRS-broth, then gently rubbing the stick on the skin or epithelial surface. Finally the swab was immersed in a sample tube containing MRS-broth. Samples were obtained according to the following scheme:

Sample 0: A blank sample was obtained in the evening before entering the study comprising LB931 bacteria. Evening, day 1; a panty liner was put on.

Sample 1: Morning, day 2. A new panty liner is worn during the day;

Sample 2: A sample was taken in the evening before an optional bath and before putting on a new panty liner. Evening, day 2;

Sample 3: Same procedure as for sample 1. Morning, day 3;

Sample 4: Same procedure as for sample 2. Evening, day 3;

Sample 5: Same procedure as for sample 1. Morning, day 4;

Sample 6: A sample is taken in the evening before an optional bath. No panty liner is worn during the night. Evening, day 4;

Sample 7: A sample is taken in the morning day 5. No panty liner is worn during the day.

Sample 8: The last sample is taken in the evening day 5.

Figure 3:
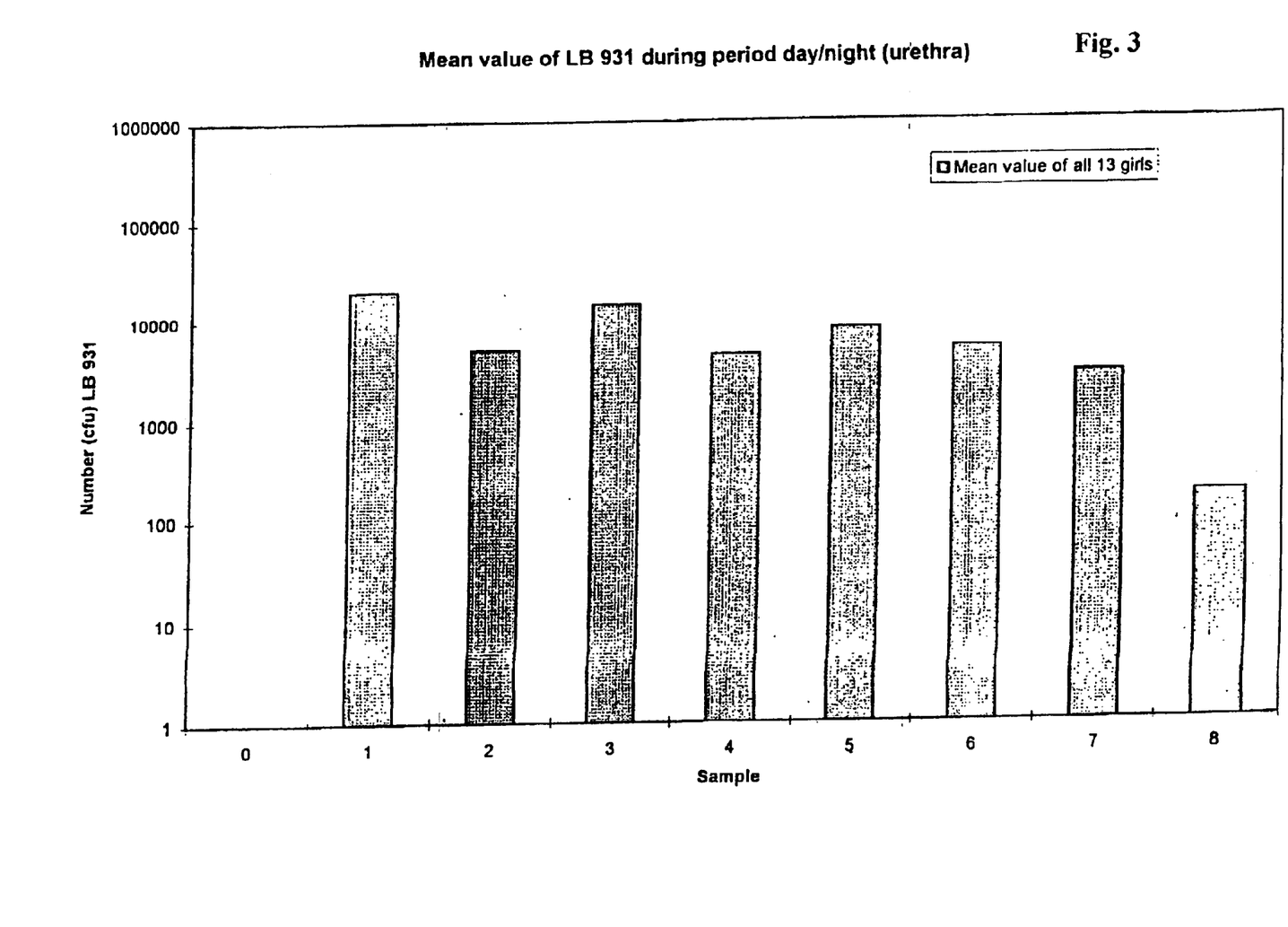
FIGS. 3 and 4 disclose the amount of LB931 transferred to the urethral orifice and perneal skin in young girls after using a panty liner comprising LB931.
Figure 4:
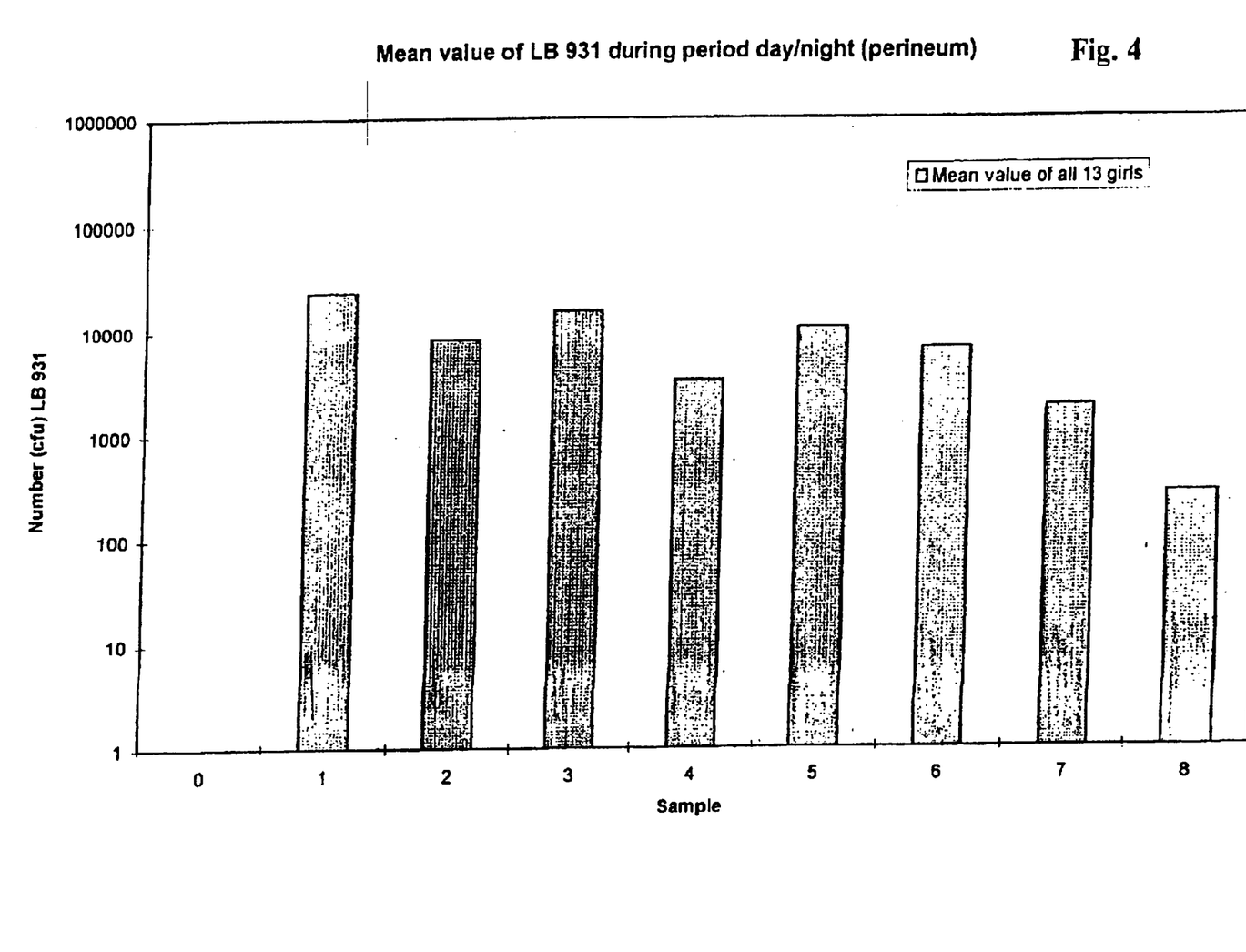

The results are presented in FIG. 3 (urethral orifice) and FIG. 4 (Perineum skin). The results show that LB931 can be transferred from an absorbent article.

EXAMPLE 6

Sensitivity to Antibiotics and Spermacidal Agents

MIC values of *Lactobacillus plantarum* LB931 were determined using E-test (Brown et al. J Antimicrob Chemother 1991;27:185–190). The results are disclosed in table V below.

TABLE V

| Antibiotic substance | MIC µg/ml |
|---|---|
| Ampicillin | 0.19 |
| Cefotaxime | 0.094 |
| Cefuroxime | 0.38 |
| Gentamycin | 0.25 |
| Imipenem | 0.016 |
| Metronidazole | >32 |
| Erythromycin | 0.25 |
| Vancomycin | >256 |
| Piperacin/Tazobactam | 2 |
| Tetracyclin | 2 |
| Trimetoprim | 0.016 |
| Benzylpenicillin | 0.5 |

The sensitivity to antibiotic substances was also determined using the SIR system. In table VI below S means sensitive and R strands for resistant.

TABLE VI

| Antibiotic substance | Zone (mm) | Indication |
|---|---|---|
| Cefadroxil | 24 | S |
| Clindamycin | 35 | S |
| Tri/sulfamethoazole | 43 | S |
| Ceftazidime | 35 | S |
| Amikacin | 30 | S |
| Aztreonam | 0 | R |
| Mecillinam | 0 | R |
| Nalidixin acid | 0 | R |

TABLE VI-continued

| Antibiotic substance | Zone (mm) | Indication |
| --- | --- | --- |
| Netilmycin | 0 | R |
| Nitrofuantin | 36 | S |
| Norfloxacin | 0 | R |
| Tobramycin | 32 | S |
| Mecillinam/Ampicillin | 41 | S |
| Cefipirome | 47 | S |
| Oxacillin | 0 | R |
| Cefalotin | 22 | S |

LB931 is sensitive to some antibiotics usually prescribed for urinary tract infections but LB931 is also resistant to for example Nalidixin acid and Norfloxacin. LB931 is also resistant to Vancomycin.

MIC tests were also carried out for the spermacidal agent Tergitol. LB931 was grown on MRS agar in 5% $CO_2$, 37° C. for 48 h. The bacteria were inoculated in 3 ml MRS broth and incubated for 10 h under the same conditions as previously 1.5% of the culture was reinoculated to 3 ml MRS broth and was incubated under the same conditions for 18 h. NP-9 Tergitol (Sigma, US) Lot 47F0002 was diluted in MRS broth having a temperature of 37° C. (reduced viscosity) to a stock solution of 40%. Using this stock solution, 3 ml solutions of the following concentrations were prepared: 0%; 5%; 10%; 20%; 30%; and 40%. 10 $\mu$l bacterial culture was added to each solution. The blank solution was mixed and added to MRS agar plates. The plates were grown in 5% $CO_2$, 37° C. for 48 h for determining the cell density. The rest of the solutions were incubated without mixing in 5% $CO_2$, 37° C. for 18 h. The solution containing 30% and 40% NP-9 were diluted in 37 ° C. MRS broth (reduced viscosity). All solutions were vigorously mixed; diluted in sterile 0.9% NaCl and added to MRS agar plates The plates were incubated in 5% $CO_2$, 37° C. for 48 h for determining cfu/ml.

The results are disclosed in table VII below.
Inoculated amount of LB931 was $1.0 \times 10^7$ .cfu

| Tergitol NP-9 | Cfu/ml LB931 |
| --- | --- |
| 0% | $2.6 \times 10^9$ |
| 1% | $2.5 \times 10^9$ |
| 5% | $2.5 \times 10^9$ |
| 10% | $1.6 \times 10^9$ |
| 20% | $1.4 \times 10^9$ |
| 30% | $1.0 \times 10^9$ |
| 40% | $6.9 \times 10^7$ |

The results show that LB931 is able to survive well in up to 40% tergitol NP-9.

EXAMPLE 7

Adherence of LB931 to Vaginal Epithelial Cells a) Preparation of a Suspension of LB931

LB931 was grown on MRS agar (5% $CO_2$, 37° C.; 48 h). The culture was inoculated to 3 ml broth (5% $CO_2$; 37° C.; 8 h). 2% of the resulting culture was reinoculated to 10 ml MRS broth (5% $CO_2$; 37° C.; 18 h). The resulting culture was centrifuged for 8 min at 20° C. and at 2000 rpm in a swing-our rotor (820×g). The obtained cell pellet was washed in 5 ml lactic acid buffer (10 mM lactic acid, pH 4.5, 0.15 M NaCl). The bacteria are diluted in lactic acid buffer until $OD_{500}$ is about 1.0 (about $10^8$ cfu/ml)

b) Preparation of Vaginal Epithelial Cells

Vaginal epithelial cells were harvested using a sterile cotton stick, and the cells wear transferred to 4 ml lactic acid buffer or PBS in a small tube. The tube was mixed and the cotton stick was removed. The tube was centrifuged at 700 rpm at 20° C. for 8 min. in a Jouan CR.-12 swingout-rotor (≈100×g), and the obtained pellet was washed in 3 ml lactic acid buffer or PBS. The cells were counted in a hematocytometer and the concentration was adjusted to $10^5$–$10^6$ cells/ml by using lactic acid buffer or PBS. 25 $\mu$l cells were spread on a microscope slide for controlling the washing procedure (see below).

c) Adherence Tests 0.5 ml LB931 suspension and 0.5 ml cell suspension were briefly mixed in a 1.5 ml eppendorf tube. A control sample was prepared by mixing 0.5 ml cell suspension and 0.5 ml buffer. The tubes were centrifuged at 20° C. and 2000 rpm (≈720×g), and subsequently incubated for 1 h at 37° C. After the incubation, the tubes were centrifuged for 8 min. at 20° C. at 700 rpm (≈90×g). The pellets were washed in 1 ml lactic acid buffer or PBS. Finally, the pellet was suspended in 400–500 $\mu$l lactic acid buffer or PBS.

d) Analysis

25 $\mu$l of a suspended pellet was allowed to air-dry on a microscope slide, followed by fixation and Gram-staining. From each sample 50 epithelia cells are analysed. The number of LB931 adhered to the cells are counted and the results are divided in five groups (0–10, 11–30, 31–50, 51–100, >100 bacteria/cell).

The results are disclosed in Table VIII below:

TABLE VIII

Number of test persons: 5
Sampling occasions: Before menstruation (bm); Ovulation (Ov)

| Epithelia cells samples | Adhered LB931/epithelia cell | | | | |
| --- | --- | --- | --- | --- | --- |
| | 0–10 | 11–30 | 31–50 | 51–100 | >100 |
| (bm) incubated with LB931, pH 4.5 | 17.2* | 24.8 | 14.4 | 15.6 | 28.0 |
| (bm) incubated control cells, pH 4.5 | 99.6 | 0.4 | | | |
| (Ov) incubated with LB931, pH 4.5 | 8.4 | 22.8 | 19.2 | 20.0 | 29.6 |
| (Ov) incubated control cells, pH 4.5 | 98.4 | 1.6 | | | |

*figures are given in percent.

The results clearly shows that LB931 bacteria adhere well to vaginal epithelial cells independent when the cells are sampled.

What is claimed is:

1. A biologically pure strain of *Lactobacillus plantarum* strain LB931, said strain has been assigned accession number DSM11918.

2. A pharmaceutical composition comprising *Lactobacillus plantarum*, strain LB931, which has been deposited at Deutsche Sammlung von Mirkoorganismen, and been assigned accession number DSM11918, together with a pharmaceutically acceptable carrier and/or diluent.

3. A pharmaceutical composition according to claim 2, further comprising other lactic acid bacteria.

4. A pharmaceutical composition according to claim 2 comprising $10^4$ to $10^{11}$ colony forming units, *Lactobacillus plantarum* LB931.

5. A pharmaceutical composition according to claim 4, wherein said pharmaceutically acceptable carrier is skimmed milk, or a lactobacillus growth medium in powder form.

6. A pharmaceutical composition according to claim 2 which is a suspension, spray, gel, cream, powder, capsule or a vaginal insert.

7. The pharmaceutical composition according to claim 2, wherein said *Lactobacillus plantarum* LB931 is in an amount of $10^5$ to $10^9$ cfu.

8. An absorbent product comprising *Lactobacillus plantarum* strain LB931, said strain has been assigned accession number DSM11918.

9. An absorbent product according to claim 8, comprising $10^4$ to $10^{11}$ cfu, *Lactobacillus plantarum* LB931.

10. The absorbent product according to claim 9, wherein LB931 is an amount of $10^5$ to $10^9$ cfu.

11. The absorbent product according to claim 8, wherein said absorbent product is selected from the group consisting of a feminine hygiene product, diaper, sanitary napkin, panty guard and incontinence guard.

12. A method of preparing a pharmaceutical composition for preventing and/or treating urogenital infections, comprising:

adding *Lactobacillus plantarum*, strain LB931, said strain has been assigned accession number DSM11918 to said pharmaceutical composition.

13. The method according to claim 12, wherein said pharmaceutical composition prevents or inhibits the growth of enterobacteria.

14. The method according to claim 12, wherein said absorbent product prevents or treats the growth of enterobacteria.

15. The method according to claim 14, wherein said absorbent product is selected from the group consisting of a diaper, sanitary napkin, panty guard, incontinence guard and feminine hygiene product.

16. A method of preparing an absorbent product suitable for preventing and/or treating urogenital infections, comprising:

adding *Lactobacillus plantarum*, strain LB931, which has been deposited at Deutsche Sammlung von Mikroorganismen, and has been assigned accession number DSM11918 to said absorbent product.

17. A method for preventing and/or treating urogenital infections in a patient, comprising:

administering *Lactobacillus plantarum*, strain LB931, which has been deposited at Deutsche Sammlung von Mikroorganismen, and has been assigned accession number DSM11918 in an effective amount to said patient.

18. The method according to claim 17, wherein said *Lactobacillus plantarum* is administered to said patient via a pharmaceutical composition selected from the group consisting of ointments, creams, liquid solutions, suppositories, and capsules.

19. The method according to claim 17, wherein said *Lactobacillus plantarum* is administered to said patient by placing an absorbent product containing *Lactobacillus plantarum* in close contact with the skin of said patient, said absorbent product selected from the group consisting of a diaper, sanitary napkin, panty guard, incontinence guard and feminine hygiene product.

20. The method according to claim 19, wherein said absorbent product prevents or treats the growth of enterobacteria.

* * * * *